US010383174B2

(12) United States Patent
Louveau et al.

(10) Patent No.: US 10,383,174 B2
(45) Date of Patent: Aug. 13, 2019

(54) ELECTRONIC CIGARETTE

(71) Applicant: JT International S.A., Geneva (CH)

(72) Inventors: Eric Louveau, Antibes (FR); Didier Malcavet, Cagnes-sur-Mer (FR); Steve Anavi, Paris (FR); Alexandre Prot, Paris (FR)

( * ) Notice: Subject to any disclaimer, the term of this patent is extended or adjusted under 35 U.S.C. 154(b) by 333 days.

(21) Appl. No.: 15/120,710

(22) PCT Filed: Feb. 20, 2015

(86) PCT No.: PCT/FR2015/050416
§ 371 (c)(1),
(2) Date: Aug. 22, 2016

(87) PCT Pub. No.: WO2015/124878
PCT Pub. Date: Aug. 27, 2015

(65) Prior Publication Data

US 2017/0019951 A1 Jan. 19, 2017

(30) Foreign Application Priority Data

Feb. 21, 2014 (FR) ..................................... 14 51409

(51) Int. Cl.
*A61M 15/06* (2006.01)
*H05B 1/02* (2006.01)
(Continued)

(52) U.S. Cl.
CPC ......... *H05B 1/0208* (2013.01); *A24F 47/008* (2013.01); *G01N 27/18* (2013.01); *H05B 2203/035* (2013.01)

(58) Field of Classification Search
None
See application file for complete search history.

(56) References Cited

U.S. PATENT DOCUMENTS 6,040,560 A 3/2000 Fleischhauer et al.
2002/0079309 A1* 6/2002 Cox .................... A61M 11/041 219/486

(Continued)

FOREIGN PATENT DOCUMENTS

EP 0430566 A2 6/1991
EP 2143346 A1 1/2010

(Continued)

OTHER PUBLICATIONS

French Patent Office Search Report dated Aug. 28, 2015 for Appln. No. 1451409 (2 pages).

(Continued)

*Primary Examiner* — Thor S Campbell
(74) *Attorney, Agent, or Firm* — Lerner, David, Littenberg, Krumholz & Mentlik, LLP

(57) ABSTRACT

This electronic cigarette comprises: —a heating element able to vaporize a substrate during a smoking period; —means for measuring an approximation of a characteristic of the voltage across the terminals of the heating element during this smoking period, said approximation being measured across the terminals of a circuit no component of which exhibits intrinsic characteristics not disturbed by the inhalations; —means of estimating an approximation of said characteristic of the voltage across the terminals of the heating element in the absence of inhalation during said smoking period; means of calculating an intensity representative of the intensity of the inhalations during said smoking period on the basis of an integration of the difference between said approximations during said smoking period; and —means of estimating the said quantity of substrate vaporized by the heating element at least on the basis of said intensity.

9 Claims, 8 Drawing Sheets

(51) Int. Cl.
*A24F 47/00* (2006.01)
*G01N 27/18* (2006.01)

(56) References Cited

U.S. PATENT DOCUMENTS

2004/0129793 A1* 7/2004 Nguyen ............... A61M 11/041 239/13
2009/0033293 A1* 2/2009 Xing ..................... H02J 7/0077 320/164
2011/0036346 A1* 2/2011 Cohen ............... A61M 15/0065 128/200.14
2011/0094523 A1* 4/2011 Thorens ................ A24F 47/008 131/194
2011/0155153 A1* 6/2011 Thorens ................... H05B 3/58 131/329
2012/0048266 A1* 3/2012 Alelov ................. A61M 11/005 128/202.21
2013/0306065 A1* 11/2013 Thorens ................ A24F 47/008 128/202.21
2013/0319435 A1* 12/2013 Flick ..................... A24F 47/008 131/328
2013/0340750 A1* 12/2013 Thorens ................ A24F 47/008 128/202.21
2014/0299141 A1* 10/2014 Flick .................... H05B 1/0202 131/329

FOREIGN PATENT DOCUMENTS

EP 2468116 A1 6/2012
JP 2014-501107 A 1/2014
KR 10-2014-0004656 A 1/2014
WO 2013/060781 A1 5/2013
WO 2013/098398 A2 7/2013

OTHER PUBLICATIONS

International Search Report dated May 11, 2015 for Appln. No. PCT/FR15150416 (4 pages).
Japanese Office Action for Application No. 2016-553494, dated Aug. 25, 2017 (9 pages).
Korea Office Action for Application No. 10-2016-7025323, dated Sep. 1, 2017 (6 pages).

* cited by examiner

ELECTRONIC CIGARETTE

Priority is claimed under 35 U.S.C. § 119 to French Application No. 1451409 filed on Feb. 21, 2014 and under 35 U.S.C. § 365 to PCT/FR2015/050416 filed on Feb. 20, 2015.

BACKGROUND OF THE INVENTION

The invention is located in the general field of electronic cigarettes comprising a heating element suitable for vaporizing a substrate in response to inhalations by the user, when the heating element is powered.

More specifically, the invention proposes a solution to provide for estimating the quantity of substrate vaporized by the heating element.

Solutions aiming to estimate this quantity are known, measuring the variation in the resistivity of the heating element when the temperature of this heating element varies due to inhalations.

Document EP 2 468 116 describes in particular a solution of this type in which the resistivity of a heating element is calculated from the potential difference across the terminals of this element.

Unfortunately, the variation in the resistivity of the heating element is very difficult to measure such that these solutions do not provide for accurately estimating the quantity of substrate vaporized.

OBJECT AND SUMMARY OF THE INVENTION

According to a first aspect, the invention relates to a method for estimating the quantity of substrate vaporized by a heating element in an electronic cigarette over a period of smoking.

In this document, the notion of "vaporization" is taken in the broad sense; it denotes the transformation of the substrate into gas, including at a temperature of less than 100° C.

This method includes:

- a step for measuring an approximation of a characteristic of the voltage across the terminals of the heating element over this period of smoking, this approximation being measured at the terminals of a circuit, no component of which exhibits intrinsic characteristics interfered with by the inhalations;
- a step for estimating an approximation of this characteristic of the voltage across the terminals of the heating element in the absence of inhalation over the period of smoking;
- a step for calculating an intensity representative of the inhalations over the period of smoking from an integration of the difference between said approximations over said period of smoking; and
- a step for estimating the quantity of substrate vaporized by the heating element from this intensity and possibly from other parameters.

Correspondingly, the invention relates to an electronic cigarette including:

- a heating element suitable for vaporizing a substrate over a period of smoking, characterized in that it includes:
- means for measuring an approximation of a characteristic of the voltage across the terminals of the heating element over this period of smoking, this approximation being measured at the terminals of a circuit, no component of which exhibits intrinsic characteristics interfered with by the inhalations;
- means for estimating an approximation of this characteristic of the voltage across the terminals of the heating element in the absence of inhalation over the period of smoking;
- means for calculating an intensity of inhalations over the period of smoking from an integration of the difference between said approximations over said period of smoking; and
- means for estimating said quantity of substrate vaporized by the heating element from this intensity and possibly from other parameters.

Thus, and generally, the invention proposes estimating the quantity of substrate vaporized over a period of smoking, by comparing the characteristics of the voltage across the terminals of the heating element with these characteristics in the absence of inhalation. However, very advantageously, the invention does not directly measure these characteristics, but measures estimates at the terminals of a circuit, the intrinsic characteristics of which are not interfered with by the inhalations.

By virtue of this particularly advantageous feature, the invention provides for very reliably estimating the intensity of these inhalations, and therefore considerably improving the estimate of the quantity of substrate vaporized.

Very advantageously, the abovementioned circuit, in which measurements are carried out at its terminals in order to estimate the characteristics of the voltage across the terminals of the heating element, does not itself include any heating element. This feature advantageously provides for limiting the power consumed for the detection of the quantity of substrate vaporized, such that a very large majority of the total power consumed by the electronic cigarette is used to vaporize the substrate. The device of the invention to measure the quantity of substrate vaporized by an electronic cigarette therefore does not exhibit the drawbacks of the device described in document EP 2 143 346.

In one embodiment of the invention, the determined quantity of substrate vaporized is used to estimate the quantity or quality of components inhaled by the user, for example a quantity of nicotine.

In a first variant embodiment of the invention, the variation in the voltage across the terminals of the heating element is estimated.

In a first embodiment of this first variant, an approximation of the variation in the voltage across the terminals of the heating element is calculated from voltages measured at the terminals of at least two elements, the voltages across the terminals of each of these elements giving an approximation of the voltage across the terminals of the heating element at instants that are slightly shifted in time.

In this embodiment of the invention, the electronic cigarette according to the invention includes:

- at least two elements, the voltage across the terminals of each of said elements giving an approximation of the voltage across the terminals of said heating element at instants that are slightly shifted in time, and
- means for measuring an approximation of the variation in the voltage across the terminals of the heating element from the voltages measured at the terminals of said elements.

The invention provides for following the change over time of the characteristics of the voltage across the terminals of the heating element, not with the aid of a tool which would precisely and directly follow this voltage in real time, but by creating an artificial delay delta between two elements of the electronic cigarette, this delay providing for obtaining at an instant t an estimate of the change in voltage across the terminals of the heating means between the instant t-delta and the instant t.

In one embodiment, these elements are series RC circuits connected in series.

In a second embodiment of this first variant, the approximation of the variation in the voltage across the terminals of the heating element is the time derivative of a potential difference measured at the terminals of a measurement resistance connected in series with the heating element.

In a second variant embodiment of the invention, the voltage across the terminals of the heating element is estimated.

In one embodiment of this second variant, the approximation of the voltage across the terminals of the heating element is the voltage measured at the terminals of a measurement resistance connected in series with said heating element.

In this embodiment, the electronic cigarette includes means suitable for measuring a potential difference across the terminals of a measurement resistance connected in series with the heating element, and means for measuring an approximation of the variation in the voltage across the terminals of the heating element from said potential difference.

BRIEF DESCRIPTION OF THE DRAWINGS

Other features and advantages of the present invention will emerge from the description given below, with reference to the accompanying drawings which illustrate an example embodiment thereof lacking any limiting character. In these drawings.

DETAILED DESCRIPTION OF A FIRST EMBODIMENT OF THE INVENTION

Figure 1:
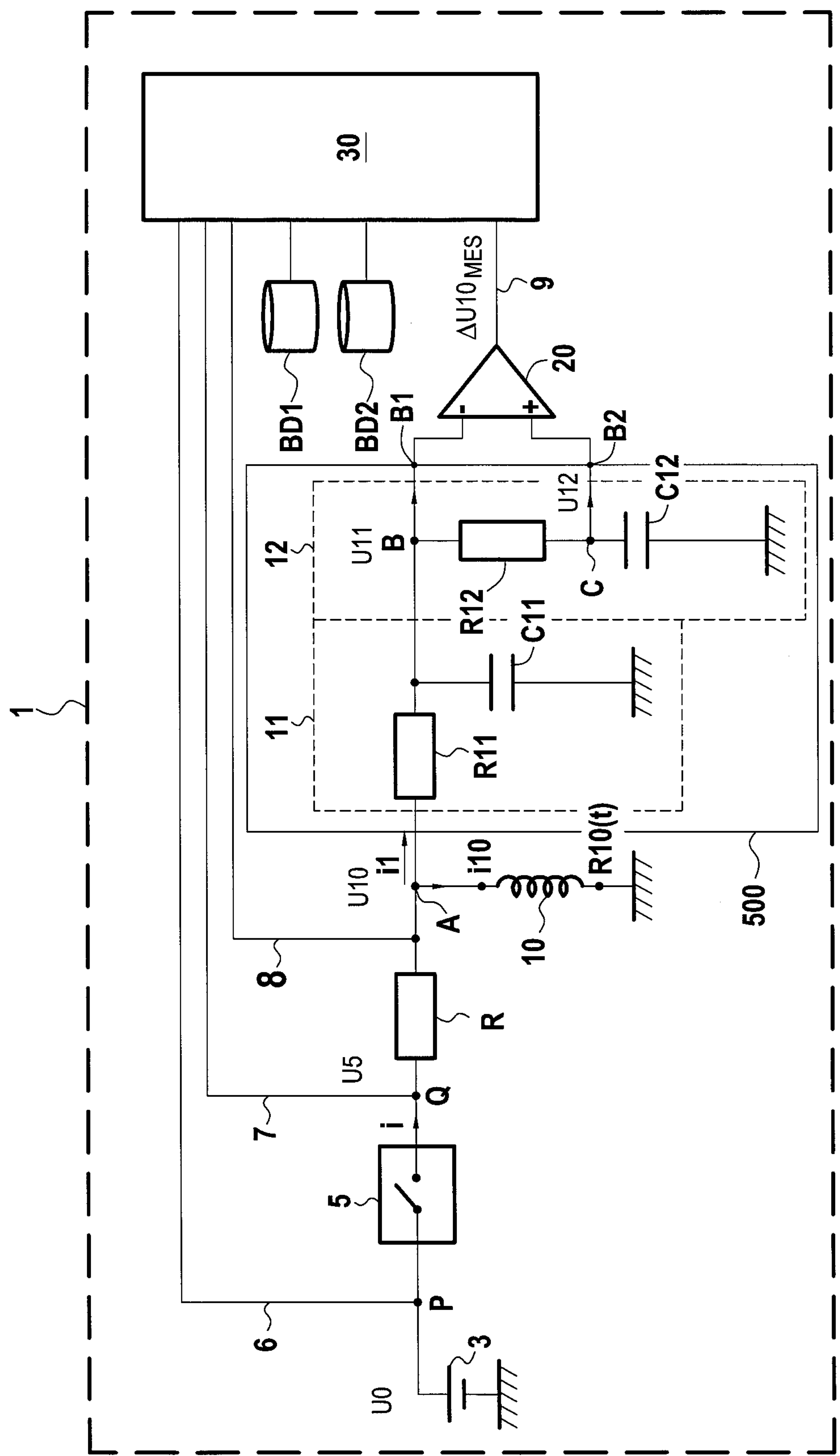
FIG. 1 represents a first embodiment of an electronic cigarette in accordance with the invention.

There will now be described, with reference to FIG. 1, a first embodiment of an electronic cigarette 1 in accordance with the invention, in which figure only the electronic components useful to the understanding of this embodiment have been represented.

The electronic cigarette 1 includes a heating element 10 suitable for vaporizing a substrate, the resistivity R10(t) of this heating element being capable of varying as a function of its temperature.

In this embodiment, the heating element 10 includes a first terminal, not referenced, connected to ground and a second terminal A, such that the potential U10 of this terminal corresponds to the voltage across the terminals of the heating element 10.

In accordance with the invention, the electronic cigarette 1 includes a battery 3 suitable for delivering a voltage U0, and a switch 5 connected to a terminal P of the battery, in order to power, only when the user presses a button, not represented, the heating element 10 from the battery 3.

In the embodiment described here, the voltage U0 exhibits a nominal voltage of the order of 3.7 V and a discharge curve in a range [4.2 V, 0 V].

When the switch 5 is in the closed position, an electrical current of intensity i passes through this switch and an electrical current of intensity i10 passes through the heating element 10.

So as to be able to measure the variations in the voltage U10(t) across the terminals of the heating element 10, the electronic cigarette 1 includes, in this embodiment, a measurement resistance R placed in series between a terminal Q of the switch 5 and the terminal A of the heating element 10. The electrical current of intensity i passes through the measurement resistance when the switch 5 is in the closed position. The intrinsic characteristics of the measurement resistance R are not interfered with by the inhalations.

Due to this particular arrangement, and considering that the switch 5 is a perfect switch (i.e. lossless, therefore U5=U0), the following is obtained in a known manner:

$$U10(t)=U0\cdot R10(t)/(R+R10(t)) \quad (1)$$

Consequently, variations in the resistivity R10(t) of the heating element 10 are accompanied by a variation in the voltage U10(t) across the terminals of the heating element.

Figure 2:
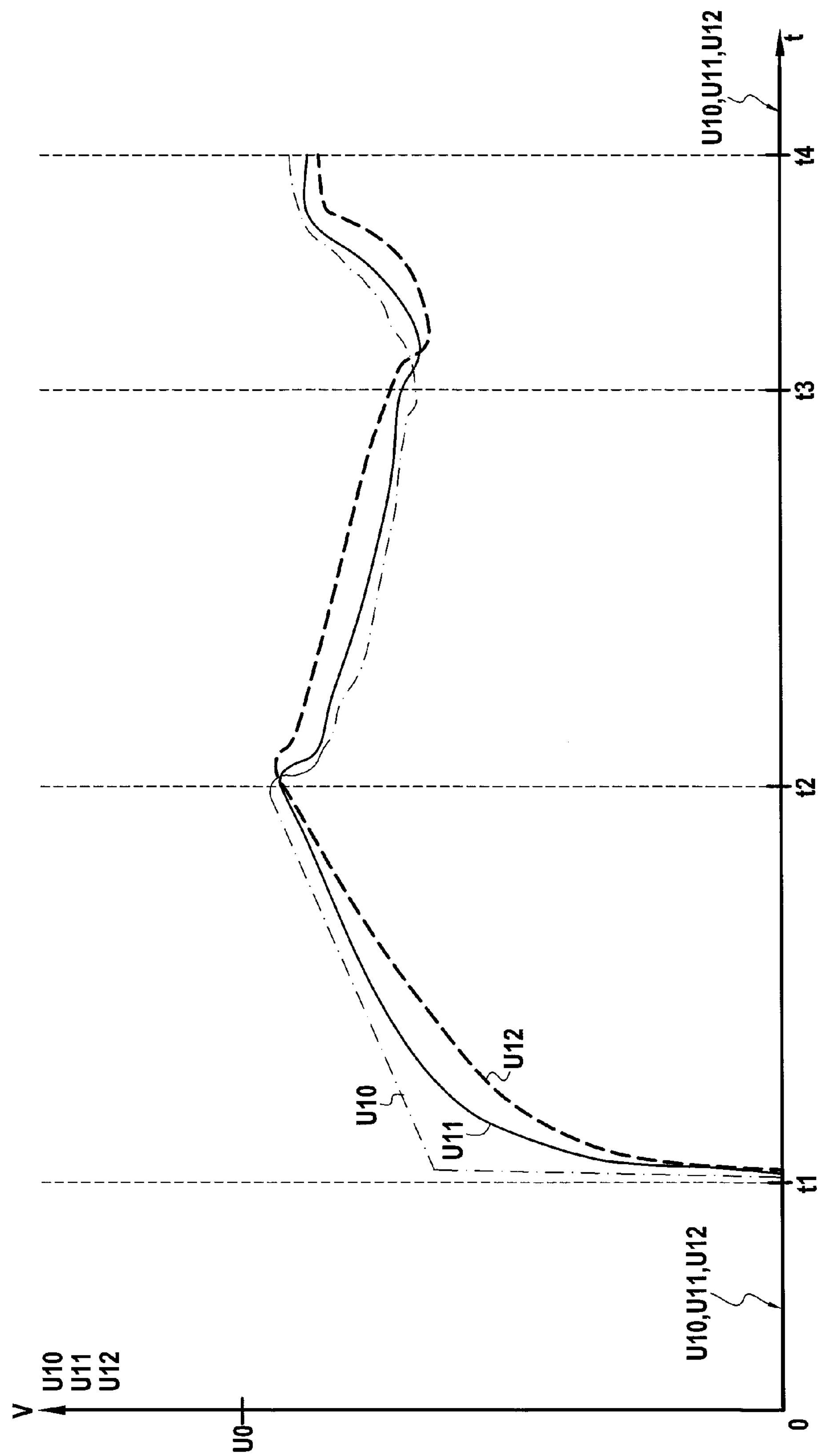
FIG. 2 represents the variation in voltage across the terminals of various components of the electronic cigarette of FIG. 1 following an inhalation.

FIG. 2 represents on the ordinate the voltage U10(t) across the terminals of the heating element 10 as a function of time, in which figure four events occurring at instants t1 to t4 have been represented:

- t1: press of the button closing the switch 5. The voltage U10(t) across the terminals of the heating element 10 which was zero almost instantaneously reaches a voltage very close to the voltage U0 of the battery 3. From this instant t1 and as long as the user does not inhale, the temperature of the heating element 10 increases until it reaches a limit temperature, its resistivity R10(t) increases and the voltage U10(t) increases.
- t2 and t3: start and stop of inhalation. Inhalation brings a flow of cold air over the heating element 10 having the effect of lowering its temperature, reducing its resistivity R10(t) and therefore lowering the voltage U10(t) across its terminals. Conversely, the end of the inhalation brings about, if the switch 5 is held closed, a reheating of the heating element and an increase in the voltage across its terminals.
- t4: release of the button and opening of the switch 5: the heating element 10 is no longer powered by the battery 3 and the voltage U10(t) across its terminals becomes zero again almost instantaneously.

In this document, "period of smoking" refers to the time period between the instants t1 and t4, i.e. the period over which the user presses the button commanding the switch 5 into the closed position. During this period, the user can if necessary not inhale, or inhale one or several puffs.

In this first particular embodiment of the invention, the quantity of substrate vaporized over a period of smoking is estimated by comparing a measurement $\Delta U10_{MES}(t)$ of an approximation of the variation in the voltage U10(t) across the terminals of the heating element 10 over this period of smoking with a theoretical estimate $\Delta U10_{TH}(t)$ of this approximation of this variation in voltage in the absence of any inhalation over this period of smoking.

More specifically, in this embodiment of the invention, there is chosen, as an approximation of the variation in voltage at instant t across the terminals of the heating element 10, the difference between two voltages U11(t) and U12(t) measured at the terminals B1, B2 of a circuit 500 comprising two subcircuits 11, 12 that are distinct and of the same type, the voltages U11(t) and U12(t) across the terminals of this circuit 500 being approximations of the voltage U10(t) across the terminals of the heating element 10 at two instants that are slightly shifted in time.

It is fundamental to observe that none of the components of the circuit 500 has intrinsic characteristics interfered with by the inhalations.

In the embodiment described here, two series RC subcircuits 11, 12 are used, placed in series between the heating element 10 and calculation means 30 suitable for calculating the difference between the voltages U11(t) and U12(t).

In the embodiment described here, the voltages U11(t) and U12(t) are the potentials of points B and C represented in FIG. 1.

The time constant T12 of the second RC circuit 12 is chosen to be much greater than the time constant T11 of the first RC circuit 11, for example by a factor of 100.

In the embodiment described here, an amplifier 20 of gain G is used to amplify the difference ΔU10(t) between U11(t) and U12(t).

In the embodiment described here, the resistances R11 and R12 of the RC subcircuits 11 and 12 are negligible with respect to the impedance of the amplifier 20.

Consequently, $$\Delta U10(t)=G\cdot(U12(t)-U11(t))$$

In the embodiment described here:

- the gain G is chosen to be in the range [100; 10000], for example equal to 500;
- the difference U12(t)−U11(t) is of the order of a few tens of microvolts; and
- ΔU10(t) is of the order of a few tens, even hundreds, of microvolts, and can be measured by the calculation means 30.

In FIG. 2, the output voltages U11(t) and U12(t) of the series RC subcircuits 11 and 12 are also represented.

As explained previously, when the user presses the button at instant t1, the heating element 10 is powered and the voltage U10(t) across its terminals increases. The two capacitances C11, C12 of the RC subcircuits 11, 12 charge up, the second and higher-value capacitance C12 being in delay with respect to the first and lower-value capacitance C11. Consequently, it is observed between pressing the button (t1) and starting inhalation (t2) that U12(t)<U11(t)<U10(t).

When the user starts to inhale at instant t2, the heating element 10 cools and the voltage U10(t) across its terminals reduces. The second and higher-value capacitance C12 is in delay with respect to the first and lower-value capacitance C11. It is observed over the entire duration of the inhalation, i.e. between t2 and t3, that U12(t)>U11(t)>U10(t).

When the user stops inhaling at instant t3, the heating element 10 heats up again and the voltage U10(t) across its terminals increases. There is then a return to the situation in which: U12(t)<U11(t)<U10(t).

Shortly after the user releases the button at instant t4, the voltage U10(t) becomes zero again, the capacitances C11 and C12 discharge and their output voltages U11(t), U12(t) become zero again.

In a known way, a distinction is drawn, when a constant voltage is applied across the terminals of a capacitance, between a transient state during which the capacitance charges up gradually until it reaches a limit charge depending on its value, and a steady state during which the charge of the capacitance remains at this limit value as long as this constant voltage is continued to be applied to it.

FIG. 2 corresponds to the situation in which the user begins to inhale (instant t2) in the steady state. The person skilled in the art will understand that if the user began to inhale during the transient state, since the high-value capacitance C12 is not completely charged, the output voltage U12(t) of the second capacitance would not necessarily become greater than the output voltage U11(t) of the first capacitance.

In the embodiment described here, the system formed by the two subcircuits 11 and 12 is in the transient state for about 800 ms after instant t1 at which the user presses the button.

Figure 3:
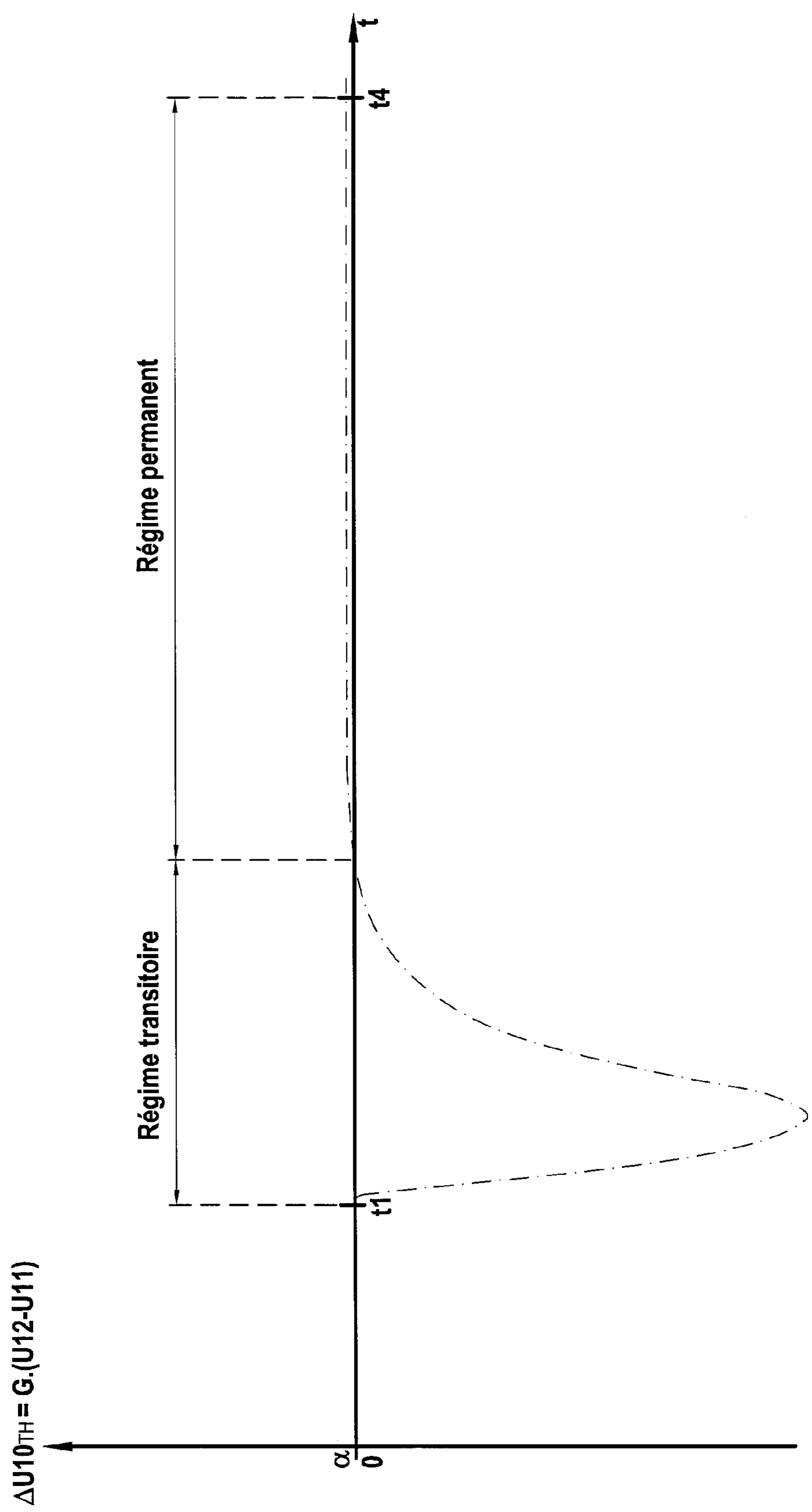
FIG. 3 represents the theoretical difference between the output voltages of two RC circuits of FIG. 1, in the absence of inhalation.

FIG. 3, which represents the theoretical difference $\Delta U10_{TH}(t)$ between the output voltages U11(t) and U12(t) of the two RC subcircuits 11, 12 in the absence of inhalation, in other words a theoretical approximation of the variation in the voltage U10(t) across the terminals of the heating element 10 at the instant t, illustrates these different states.

During the transient state, U12(t) is always less than U11(t) but, as represented in FIG. 2, the absolute value of the difference between these two voltages increases then decreases until it reaches a constant value a in the steady state.

In the embodiment described here, this constant α can be neglected and is assumed to be zero hereafter.

In the transient state, and noting:

- R11, the resistance of the first series RC subcircuit 11;
- C11, the capacitance of the first series RC subcircuit 11;
- R12, the resistance of the second series RC subcircuit 12;
- C12, the capacitance of the second series RC subcircuit 12;
- T11, the time constant R1·C1 of the first series RC subcircuit 11; and
- T12, the time constant R2·C2 of the second series RC subcircuit 12; the following is theoretically obtained:

$$U11_{TH}(t)=U10(t)\cdot(1-\exp(-t/T11))$$

$$U12_{TH}(t)=U11_{TH}(t)\cdot(1-\exp(-t/T12))$$

$$\text{i.e. } U12_{TH}(t)=U10(t)\cdot(1-\exp(-t/T11))\cdot(1-\exp(-t/T12))$$

Consequently, the theoretical variation $\Delta U10_{TH}(t)$ in the voltage across the terminals of the heating element 10 is expressed as:

$$\Delta U10_{TH}(t)=G\cdot(U11_{TH}(t)-U12_{TH}(t))$$

$$\text{i.e. } \Delta U10_{TH}(t)=G\cdot U10(t)\cdot(1-\exp(-t/T11))\cdot(\exp(-t/T12))$$

or with (1):

$$\Delta U10_{TH}(t)=G\cdot[U0\cdot R10(t)/(R+R10(t))]\cdot(1-\exp(-t/T11))\cdot(\exp(-t/T12))$$

By making the approximation that R10(t) is constant over the period of smoking and equal to R10(t1), the expression for $\Delta U10_{TH}(t)$ is finally obtained:

in the transient state:

$$\Delta U10_{TH}(t)=G\cdot[U0\cdot R10(t1)/(R+R10(t1))]\cdot(1-\exp(-t/T11))\cdot(\exp(-t/T12)) \quad (2)$$

in the steady state:

$$\Delta U10_{TH}(t)=\alpha=0.$$

In the embodiment of FIG. 1, the approximation $\Delta U10_{MES}(t)$ of the variation in the voltage U10(t) across the terminals of the heating element 10 is the output voltage of the amplification means 20, i.e. the potential of the terminal 9.

In the embodiment described here, the quantity of substrate vaporized over a period of smoking is estimated from an intensity of inhalation F calculated by integrating the difference over a period of smoking, between the approximation $\Delta U10_{MES}(t)$ of the variation in the voltage U10(t) across the terminals of the heating element 10 over this period of smoking and the theoretical estimate $\Delta U10_{TH}(t)$ of this approximation of this variation in voltage in the absence of any inhalation over the period of smoking.

Figure 4:
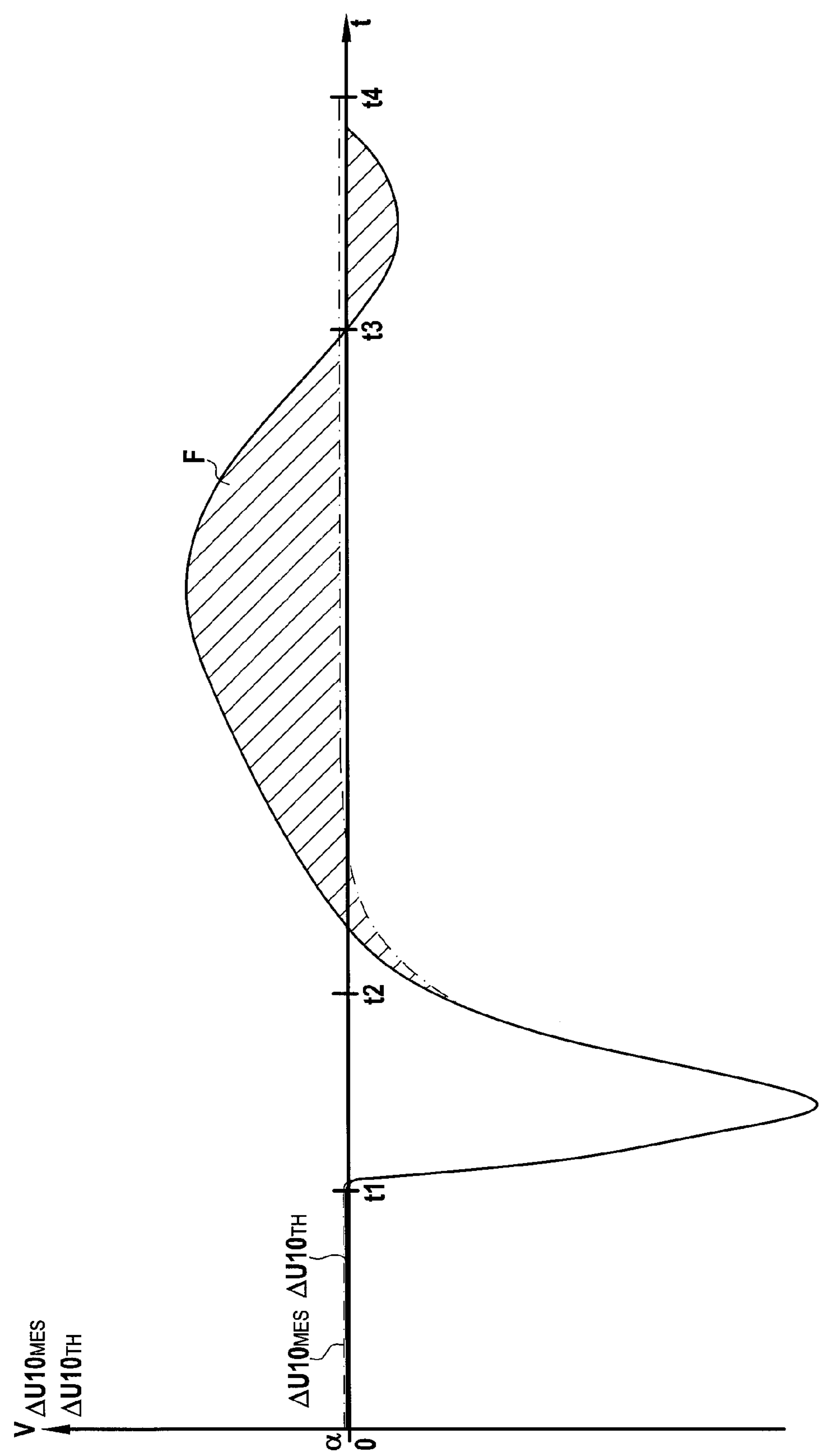
FIG. 4 illustrates a method for calculating an intensity of inhalation in the electronic cigarette of FIG. 1.

This intensity of inhalation F corresponds, in the example embodiment described here, to the hatched area in FIG. 4. This area can notably be calculated by a Riemann sum with an interval of 20 ms between the instants t2 and t4.

In the example embodiment described here, t2 is determined as being the instant at which the absolute value of the difference $\Delta U10_{MES}(t)$ and $\Delta U10_{TH}(t)$ becomes greater than a predetermined threshold $S_{T2}$:

$$|\Delta U10_{MES}(t2)-\Delta U10_{TH}(t2)|>S_{T2}$$

Instant t4 is the instant at which the user releases the button.

To calculate the intensity of inhalation F by the Riemann method, $\Delta U10_{MES}(t)$ and $\Delta U10_{TH}(t)$ are evaluated and stored at various instants between t1 and t4, for example every 20 ms. In this embodiment:

1. $\Delta U10_{MES}(t)$ is the measurement of the potential of the terminal 9 at instant t;
2. $\Delta U10_{TH}(t)$ between t1 and t1+800 ms (transient state) is read from a record of a first database BD1 constructed during preliminary tests carried out in the laboratory and stored in the electronic cigarette 1, the record being selected as a function of the parameters of equation (2).
3. $\Delta U10_{TH}(t)=0$, between t1+800 ms and t4 (steady state).

Returning to equation (2), the expression for $\Delta U10_{TH}(t)$ in the transient state is dependent on six parameters, namely:

- the gain G of the amplifier 20;
- the voltage U0 delivered by the battery 3;
- the resistivity R10(t1) of the heating element assumed to be constant;
- the value of the measurement resistance R;
- the time constants T11 and T12 of the RC subcircuits 11 and 12.

In the embodiment described here, and returning to FIG. 1, the calculation means 30 are suitable for measuring the voltage U0 at the terminal P of the battery 3 by means of a voltage probe 6.

In the embodiment described here, the calculation means 30 are also suitable for estimating the resistivity R10(t1) of the heating element. To this end, the calculation means 30 measure, at instant t1, the voltages U5 at the terminal Q of the switch 5 by means of a voltage probe 7 and the voltage U10 at the terminal A of the heating element 10 by means of a voltage probe 8.

Denoting by i the intensity of the electronic current which flows through the resistance R, application of Kirchhoff's current law at the terminal A and Ohm's law to the resistance R gives rise to: i1+i10=(U5−U10)/R.

However, in the embodiment described here, i1 is negligible next to i10. Consequently, by application of Ohm's law to the heating element 10:

$$R10=R\cdot U10/(U5-U10) \quad (3)$$

In the embodiment of the invention described here, the first database BD1 stores, for a plurality of sextuples corresponding to the six parameters {G, U0, R10, R, T11, T12}, values of the theoretical voltage $\Delta U10_{TH}(t)$ in the absence of inhalation and in the transient state at various instants t counted between t1 and t1+800 ms.

The calculation means are therefore capable of calculating the intensity of inhalation F by the Riemann method.

In the embodiment described here, the calculation means 30 query a second database BD2 of the electronic cigarette 1 in order to determine the quantity of substrate vaporized over the period of smoking as a function of four parameters:

- duration t4-t1 of the period of smoking;
- voltage U0 of the battery 3 measured by the calculation means 30;
- resistance R10(t1) of the heating element 10, assumed to be constant over a period of smoking, and measured by the calculation means 30; and
- intensity of inhalation F, calculated here by the Riemann method.

As a variant, other parameters can also be used and notably the temperature of the heating element 10 at t1, the viscosity of the substrate, the speed of evaporation of the substrate, the transfer function of the heating element 10 characterizing its cooling, the density of drops of substrate vaporized as a function of the intensity of inhalation F, etc.

In the embodiment described here, the voltage U0 of the battery 3 is measured by the calculation means 30. As a variant, this voltage could be considered to be constant and equal to the nominal value of the battery.

DESCRIPTION OF A SECOND EMBODIMENT OF THE INVENTION

In the embodiment of FIG. 1, two series RC subcircuits 11, 12 in series and an amplifier 20 are used to estimate the variation in voltage ΔU10(t) across the terminals of the heating element 10.

Figure 5:
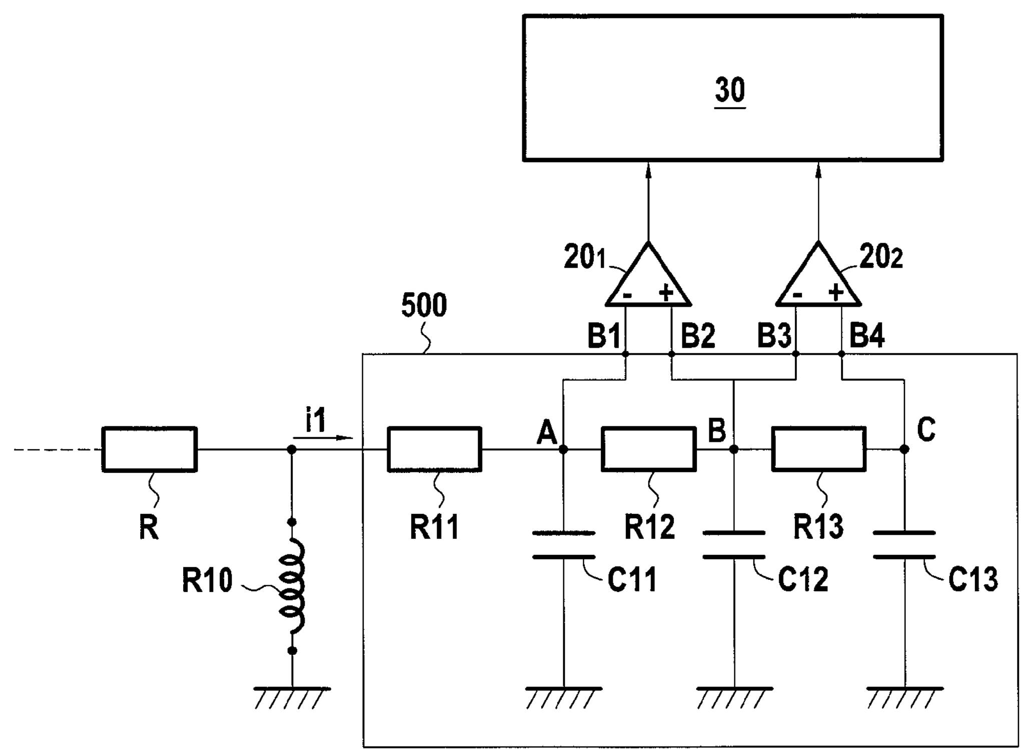
FIG. 5 represents details of an electronic cigarette in accordance with a second embodiment of the invention.

As a variant, and as represented in FIG. 5, a circuit 500 can, for example, be used, comprising three RC subcircuits and two amplifiers $20_1$, $20_2$.

In this embodiment:

- the first RC subcircuit (R11/C11) very closely follows the voltage across the terminals of the heating element R10 and represents an estimate of the voltage across the terminals of the heating element R10(t) at instant t of the measurement;
- the second RC subcircuit (R12/C12) follows with a slight delay dt the voltage across the terminals of the heating element R10 and represents an estimate of that which was the voltage R10(t-dt) across the terminals of the heating element R10 at a past instant t-dt close to instant t of the measurement;
- the third RC subcircuit (R13/C13) follows with a more significant delay Dt the voltage across the terminals of the heating element R10 and represents an estimate of that which was the voltage R10(t-Dt) across the terminals of the heating element R10 at a past instant t-Dt further away from instant t of the measurement.

To this end, the time constants of the three RC subcircuits are chosen such that the following expression is satisfied:

$$R11 \cdot C11 < R12 \cdot C12 < R13 \cdot C13;$$

Furthermore, for a finer tracking, it may be more optimal to additionally have the following expression satisfied:

$$(R11 \cdot C11)/(R12 \cdot C12) < (R12 \cdot C12)/(R13 \cdot C13)$$

None of the components of the circuit 500 have intrinsic characteristics interfered with by the inhalations.

In this embodiment, the circuit 500 exhibits four terminals B1, B2, B3 and B4.

As in the first embodiment, the quantity of substrate vaporized over a period of smoking is estimated from an intensity of inhalation F calculated by integrating the difference over a period of smoking, between the approximation of the variation in the voltage U10(t) across the terminals of the heating element 10 over this period of smoking and the theoretical estimate $\Delta U10_{TH}(t)$ of this approximation of this variation in voltage in the absence of any inhalation over the period of smoking.

However, very advantageously, in this embodiment, two approximations $\Delta U10^1_{MES}(t)$ and $\Delta U10^2_{MES}(t)$ of the variation in the voltage U10(t) across the terminals of the heating element 10 over the period of smoking are carried out, the first approximation being measured at the terminals B1 and B2 of the circuit 500, and the second approximation being measured at the terminals B3 and B4 of the circuit 500.

This embodiment provides for improving the estimate of the variations in voltage across the terminals of the heating element 10, and this regardless of the characteristics of the puff.

Indeed, by virtue of the choice of the time constants:

- the voltage measured at the terminals B1 and B2 of the circuit 500 is particularly representative of the voltage across the terminals of the heating element R10 for a certain type of inhalation, for example a fast and/or intense or irregular inhalation; while
- the voltage measured at the terminals B3 and B4 of the circuit 500 is particularly representative of the voltage across the terminals of the heating element R10 for another type of inhalation, for example a slow and/or light or continuous inhalation.

Hence, in this embodiment, the following two curves $\Delta U10_{MES}(t)$ and $\Delta U10_{TH}(t)$ are constructed:

$$\Delta U10_{MES}(t) = K1 \Delta U10^1_{MES}(t) + K2 \Delta U10^2_{MES}(t)$$

$$\Delta U10_{TH}(t) = K1 \Delta U10^1_{TH}(t) + K2 \Delta U10^2_{TH}(t)$$

where $\Delta U10^1_{TH}(t)$ and $\Delta U10^2_{TH}(t)$ are theoretical estimates of approximations $\Delta U10^1_{MES}(t)$ and $\Delta U10^2_{MES}(t)$ in the absence of any inhalation over the period of smoking.

Hence, to calculate the intensity F of the inhalation, the area between these two curves $\Delta U10_{MES}$ and $\Delta U10_{TH}$ is retained.

The coefficients K1 and K2 are fixed and determined as a function of the time constants of the RC circuits (the values R11·C11, R12·C12 and R13·C13).

In a nonlimiting manner, this pair of coefficients could be chosen in accordance with one of the four following examples:

Example 1

$$K1 = 1/2;$$

$$K2 = 1/2$$

Example 2

$$K1 = (R11 \cdot C11 + R12 \cdot C12)/(R11 \cdot C11 + 2 \cdot R12 \cdot C12 + R13 \cdot C13);$$

$$K2 = (R12 \cdot C12 + R13 \cdot C13)/(R11 \cdot C11 + 2 \cdot R12 \cdot C12 + R13 \cdot C13)$$

Example 3

$$K1 = R12 \cdot C12/(R11 \cdot C11)/((R12 \cdot C12)/(R11 \cdot C11) + (R13 \cdot C13)/(R12 \cdot C12));$$

$$K2 = R13 \cdot C13/(R12 \cdot C12)/((R12 \cdot C12)/(R11 \cdot C11) + (R13 \cdot C13)/(R12 \cdot C12))$$

Example 4

$$K1 = (R12 \cdot C12 - R11 \cdot C11)/(R13 \cdot C13 - R11 \cdot C11);$$

$$K2 = (R13 \cdot C13 - R12 \cdot C12)/(R13 \cdot C13 - R11 \cdot C11)$$

To ensure correct operation, these coefficients can be tested/validated in the laboratory.

DESCRIPTION OF A THIRD EMBODIMENT OF THE INVENTION

Figure 6:
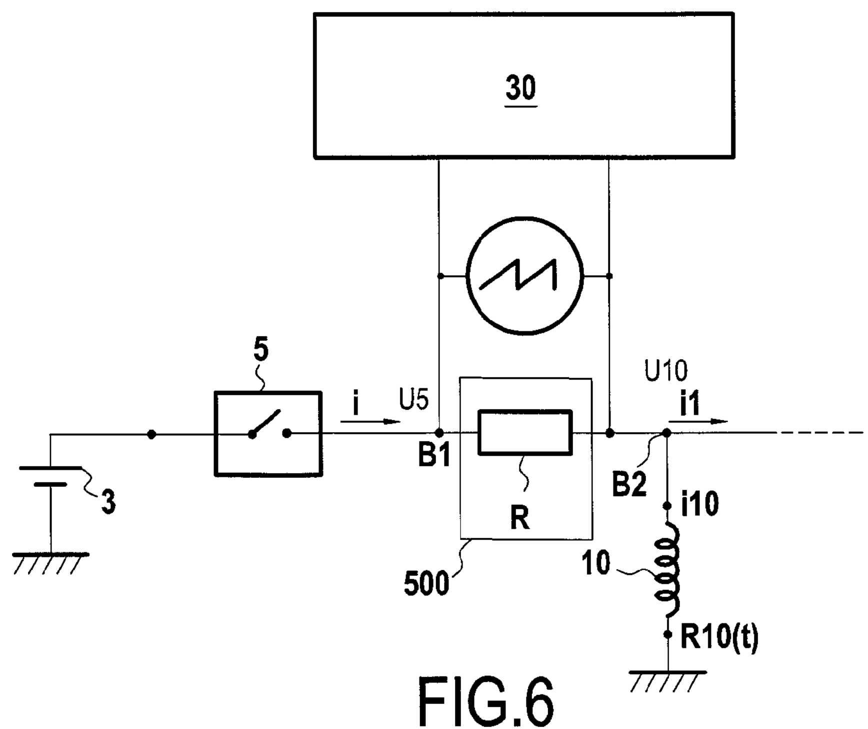
FIG. 6 represents details of an electronic cigarette in accordance with a third embodiment of the invention.
Figure 7:
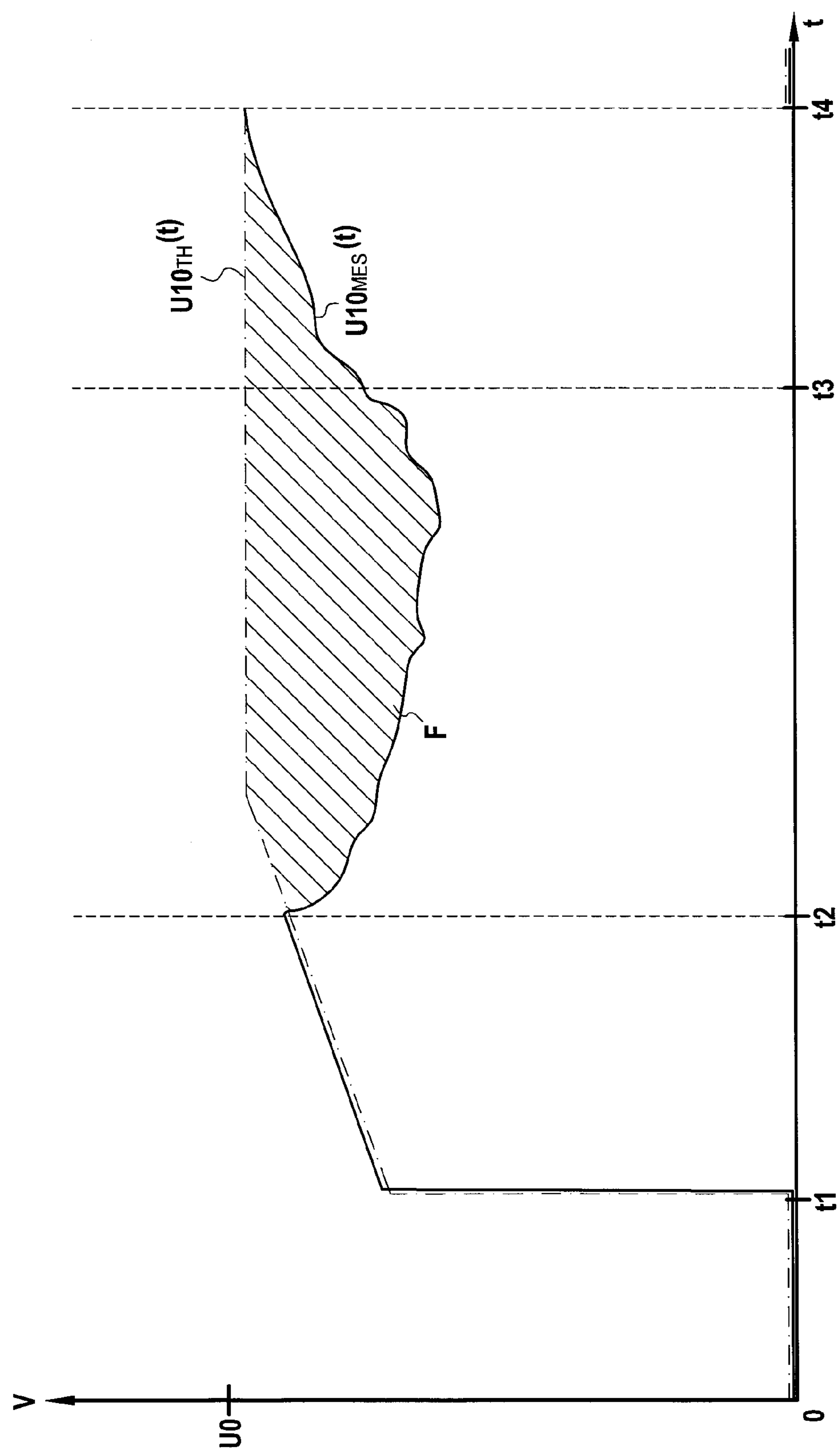
FIG. 7 illustrates a method for calculating an intensity of inhalation in the electronic cigarette of FIG. 6.

In the embodiment of FIG. 6, the variable for the voltage across the terminals of the heating element which is estimated is not the variation ΔU10(t) of this voltage but the value U10(t) of this voltage itself.

In this embodiment of the invention, this value U10(t) is estimated by measuring the voltage U5-U10 across the terminals B1 and B2 of a circuit 500 formed in this example by the measurement resistance R.

Specifically, from equation (3):

$$U10(t) = R10/R \cdot (U5 - U10)(t) \quad (4)$$

This embodiment requires the calculation means 30 to be connected to the terminals B1 and B2 of the measurement resistance R in order to precisely measure the variations of U5-U10.

FIG. 7 represents:

- the approximation $U10_{MES}(t)$ of the voltage U10(t) across the terminals of the heating element 10 over the period of smoking, calculated by using equation (4), the difference of (U5-U10)(t) being the difference of the potentials measured by the calculation means 30 of FIG. 6 between the points B1 and B2;
- the estimate of the approximation $U10_{TH}(t)$ across the terminals of the heating element 10 in the absence of inhalation over said period of smoking;
- the intensity F of the inhalation corresponding to the integration of the difference between $U10_{MES}(t)$ and $U10_{TH}(t)$ over the period of smoking.

DESCRIPTION OF A FOURTH EMBODIMENT OF THE INVENTION

Figure 8:
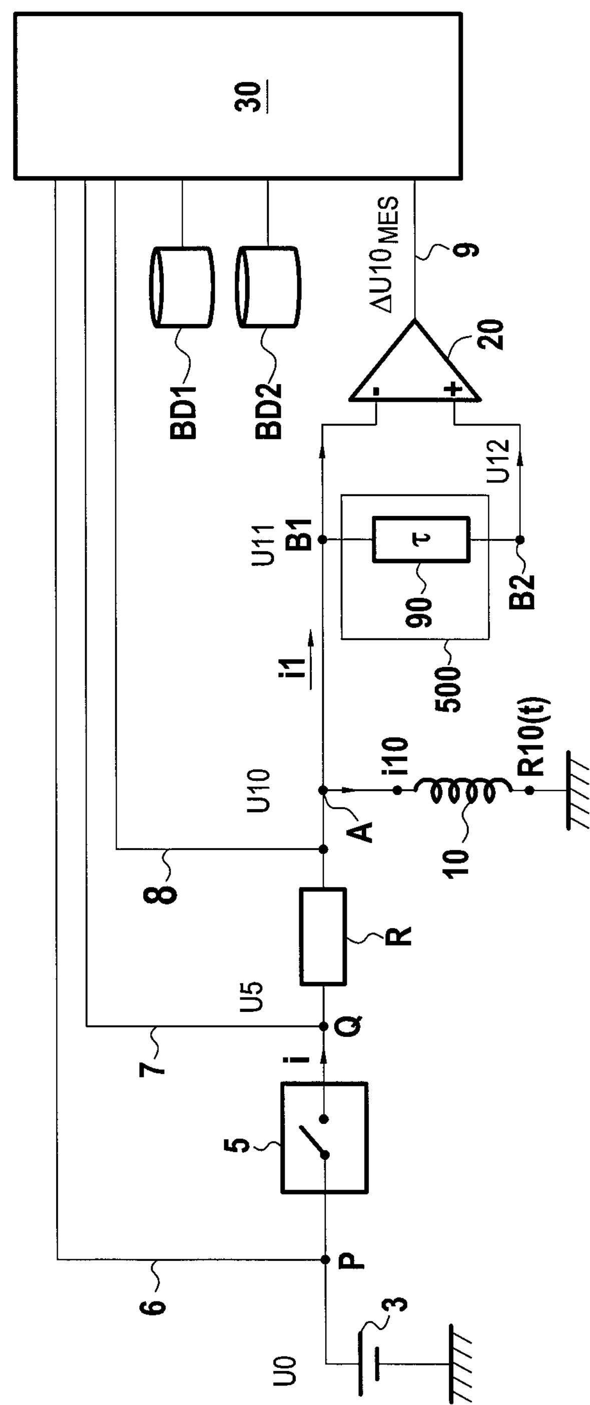
FIG. 8 represents details of an electronic cigarette in accordance with a fourth embodiment of the invention.

In a fourth embodiment represented in FIG. 8, in order to estimate the variation $\Delta U_{MES}10(t)$ in the voltage across the terminals of the heating element 10, as for the first embodiment, the difference between two voltages U12(t) and U11(t) at the terminals B1 and B2 of a circuit 500 is executed, each of these voltages giving an approximation of the voltage across the terminals of the heating element (10) at instants that are slightly shifted in time.

In this embodiment, to generate this delay, a circuit 500 is used, formed by a delay line 90 between the measurement points for the voltages U11(t) and U12(t).

This delay line can for example be formed by:

a large capacitance;

an analog-digital converter coupled to a digital-analog converter.

The intrinsic characteristics of the delay line 90 are not interfered with by the inhalations.

DESCRIPTION OF A FIFTH EMBODIMENT OF THE INVENTION

In a fourth embodiment of the invention, the variation $\Delta U_{MES}10(t)$ in the voltage across the terminals of the heating element 10 can also be estimated, by calculating the time derivative of the measured voltage $U10_{MES}(t)$, as in the third embodiment, with the calculation means 30 of FIG. 6 between the points B1 and B2.

This value can be compared with the theoretical variation $\Delta U_{TH}10(t)$ of the voltage across the terminals of the heating element 10 in the absence of inhalation, as in the first embodiment.

Figure 9:
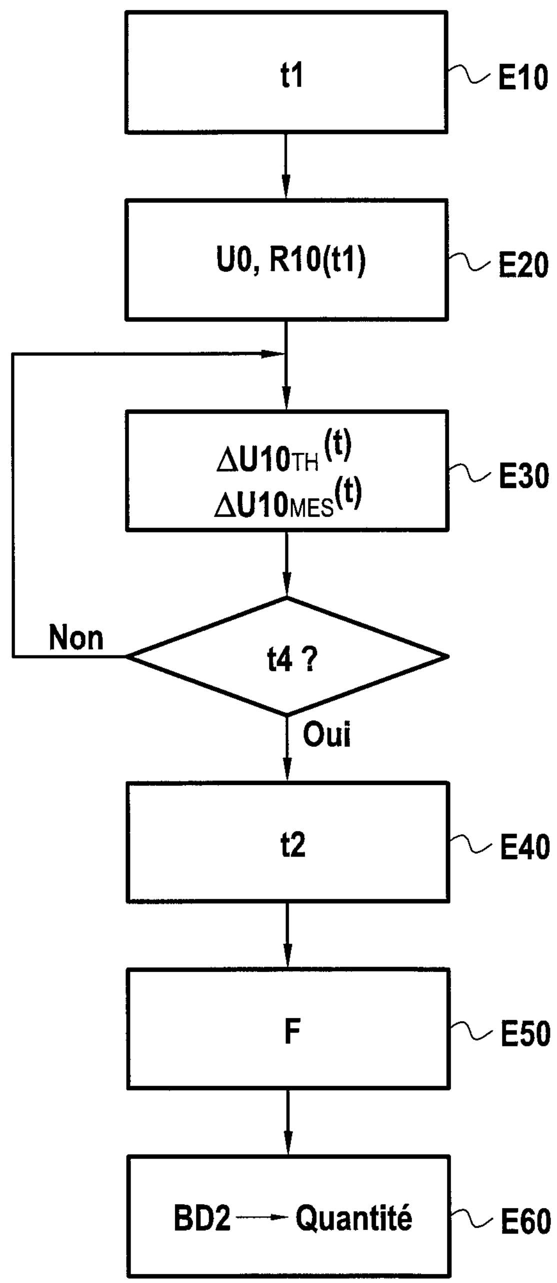
FIG. 9 represents, in the form of a flow chart, the main steps of an estimating method in accordance with a particular embodiment of the invention.

FIG. 9 represents in the form of a flow chart a method for estimating the quantity of substrate vaporized in accordance with a particular embodiment of the invention.

This method can for example be implemented by the calculation means 30 of the electronic cigarette of FIG. 1.

During a step E10, the calculation means 30 detect the press of the button bringing about the closure of the switch 5. Instant t1 of this detection is saved in memory.

During a step E20, just after this detection, the calculation means 30 measure the voltage U0 delivered by the battery 3 and the resistivity R10(t1) of the heating element.

Every 20 ms, during a step E30, until instant t4 of detection of the release of the button bringing about the opening of the switch 5, the calculation means 30:

measure $\Delta U10_{MES}(t)$ (potential of the terminal 9);

estimate $\Delta U10_{TH}(t)$ by reading the first database BD1 between t1 and t1+800 ms. Between t1+800 ms and t4, they estimate $\Delta U10_{TH}(t)=0$.

During a step E40, the calculation means 30 estimate instant t2 of the start of the puff, this instant being the first instant after t1 such that $|\Delta U10_{MES}(t2)-\Delta U10_{TH}(t2)|>S_{T2}$.

During a step E50, the calculation means 30 calculate the intensity F of the inhalation as the integration of the difference between $\Delta U10_{MES}(t)$ and $\Delta U10_{TH}(t)$ between t2 and t4.

During a step E60, the calculation means 30 estimate the quantity of substrate vaporized between t2 and t4 by querying the second database B2.

The invention claimed is:

1. A method for estimating the quantity of substrate vaporized by a heating element in an electronic cigarette over a period of smoking, characterized in that it includes:

a step for determining an approximation of a characteristic of a voltage across the terminals of the heating element over this period of smoking, said approximation being measured at the terminals of a circuit connected to the heating element, no component of which exhibits intrinsic characteristics interfered with by the inhalations;

a step for estimating an approximation of said characteristic of the voltage across the terminals of the heating element in the absence of inhalation over said period of smoking;

a step for calculating an intensity of inhalations over said period of smoking from an integration of the difference between said approximations over said period of smoking; and a step for estimating said quantity of substrate vaporized by the heating element at least from said intensity, wherein the characteristic of said voltage is a voltage at a given instant or a variation of a voltage at a given instant.

2. The estimating method as claimed in claim 1, characterized in that the approximation of the variation in the voltage across the terminals of the heating element is calculated from voltages measured at the terminals of at least two elements, the voltages across the terminals of each of said elements giving an approximation of the voltage across the terminals of said heating element at instants that are slightly shifted in time.

3. The estimating method as claimed in claim 2, characterized in that said elements are series RC circuits connected in series.

4. The estimating method as claimed in claim 1, characterized in that the approximation of the variation in the voltage across the terminals of the heating element is the time derivative of a potential difference measured at the terminals of a measurement resistance connected in series with said heating element.

5. The estimating method as claimed in claim 1, characterized in that the approximation of the characteristic of the voltage across the terminals of the heating element is determined from the voltage measured at the terminals of a measurement resistance connected in series with said heating element.

6. An electronic cigarette including a heating element suitable for vaporizing a substrate over a period of smoking, characterized in that it includes:

means for determining an approximation of a characteristic of a voltage across the terminals of the heating element over this period of smoking, said approximation being measured at the terminals of a circuit connected to the heating element, no component of which exhibits intrinsic characteristics interfered with by the inhalations;

means for estimating an approximation of said characteristic of the voltage across the terminals of the heating element in the absence of inhalation over said period of smoking;

means for calculating an intensity of inhalations over said period of smoking from an integration of the difference between said approximations over said period of smoking; and means for estimating said quantity of substrate vaporized by the heating element at least from said intensity, wherein the characteristic of said voltage is a voltage at a given instant or a variation of a voltage at a given instant.

7. The electronic cigarette as claimed in claim 6, characterized in that it includes:

at least two elements, the voltage across the terminals of each of said elements giving an approximation of the voltage across the terminals of said heating element at instants that are slightly shifted in time, and means for measuring an approximation of the variation in the voltage across the terminals of the heating element from the voltages measured at the terminals of said elements.

8. The electronic cigarette as claimed in claim 7, characterized in that said circuits are series RC circuits connected in series.

9. The electronic cigarette as claimed in claim 6, characterized in that it includes calculation means suitable for measuring a potential difference across the terminals of a measurement resistance connected in series with the heating element, and means for measuring an approximation of the variation in the voltage across the terminals of the heating element from said potential difference.

* * * * *